United States Patent
Zhou et al.

(10) Patent No.: US 10,470,816 B2
(45) Date of Patent: Nov. 12, 2019

(54) MULTI-FUNCTION HIGH-FREQUENCY TOOL FOR ENDOSCOPE

(71) Applicant: ANREI MEDICAL (HANGZHOU) CO., LTD., Zhejiang (CN)

(72) Inventors: Huazhen Zhou, Zhejiang (CN); Shuren Ma, Zhejiang (CN); Zhuo Yang, Zhejiang (CN); Zhifeng Zhao, Zhejiang (CN); Rongnan Zhang, Zhejiang (CN)

(73) Assignee: ANREI MEDICAL (HANGZHOU) CO., LTD., Zhejiang (CN)

(*) Notice: Subject to any disclaimer, the term of this patent is extended or adjusted under 35 U.S.C. 154(b) by 0 days.

(21) Appl. No.: 16/062,628

(22) PCT Filed: Nov. 14, 2016

(86) PCT No.: PCT/CN2016/105626
§ 371 (c)(1),
(2) Date: Jun. 15, 2018

(87) PCT Pub. No.: WO2017/101625
PCT Pub. Date: Jun. 22, 2017

(65) Prior Publication Data
US 2018/0368909 A1   Dec. 27, 2018

(30) Foreign Application Priority Data

Dec. 15, 2015   (CN) .......................... 2015 1 0937882

(51) Int. Cl.
*A61B 18/14*   (2006.01)
*A61M 3/02*   (2006.01)
*A61B 1/00*   (2006.01)

(52) U.S. Cl.
CPC .......... *A61B 18/14* (2013.01); *A61B 1/00087* (2013.01); *A61M 3/02* (2013.01);
(Continued)

(58) Field of Classification Search
CPC .......... A61B 1/00087; A61B 12/00234; A61B 18/1447; A61B 2018/1405;
(Continued)

(56) References Cited

U.S. PATENT DOCUMENTS

| 2007/0038213 A1* | 2/2007 | Machiya ............ A61B 18/1492 606/45 |
| 2014/0207134 A1* | 7/2014 | Wake ..................... A61B 18/14 606/39 |

FOREIGN PATENT DOCUMENTS

| CN | 103110457 | 5/2013 |
| CN | 203328800 | 12/2013 |

(Continued)

OTHER PUBLICATIONS

"International Search Report (Form PCT/ISA/210)", dated Feb. 6, 2017, with English translation thereof, pp. 1-6.

*Primary Examiner* — Jaymi E Della
*Assistant Examiner* — Rachel A. Vierra
(74) *Attorney, Agent, or Firm* — JCIPRNET (57) ABSTRACT

A multi-function high-frequency tool for an endoscope, comprising an insert portion and a handle portion, the insert portion comprising an insulating tip, a first electrode having a needle-knife function, a second electrode having an IT-knife function, and a spray head; the handle portion comprising a first slider, a connector, an injection connector, and a second slider. The second electrode has a hollow structure, and the first electrode extends through the second electrode; the proximal end of the first electrode is fixedly connected by means of a mandrel connecting member to the distal end of a mandrel; the proximal end of the mandrel is connected to the first slider of the handle portion, and moves axially on the handle portion by means of the first slider, thereby causing the first electrode to expose from/retract into the second electrode.

9 Claims, 5 Drawing Sheets

(52) U.S. Cl.
CPC ............. *A61B 2018/1405* (2013.01); *A61B 2018/1452* (2013.01)

(58) Field of Classification Search
CPC ... A61B 17/00234; A61B 18/12; A61B 18/14; A61B 18/1492; A61B 2018/00482; A61B 2018/00601; A61B 2018/00607; A61B 2018/1425; A61B 2018/1475; A61B 2018/1452; A61M 3/02
See application file for complete search history.

(56) References Cited

FOREIGN PATENT DOCUMENTS

| | | |
|---|---|---|
| CN | 104055572 | 9/2014 |
| CN | 203861344 | 10/2014 |
| CN | 104411265 | 3/2015 |
| CN | 105434038 | 3/2016 |
| CN | 205307086 | 6/2016 |
| JP | 2009240380 A * | 10/2009 |
| JP | 4870710 | 2/2012 |
| JP | 5601776 | 10/2014 |

* cited by examiner

MULTI-FUNCTION HIGH-FREQUENCY TOOL FOR ENDOSCOPE

CROSS-REFERENCE TO RELATED APPLICATION

This application is a 371 application of the international PCT application serial no. PCT/CN2016/105626, filed on Nov. 14, 2016, which claims the priority benefit of China application no. 201510937882.9, filed on Dec. 15, 2015. The entirety of each of the abovementioned patent applications is hereby incorporated by reference herein and made a part of this specification.

BACKGROUND OF THE INVENTION

1. Field of the Invention

The present invention generally relates to an instrument for endoscopic submucosal dissection (ESD) to treat gastrointestinal polyps and early cancers, in particular, to a multi-function high-frequency tool for an endoscope.

2. Description of Related Art

Common electrotome knives for ESD in the market include a needle-knife, an IT knife (having a ceramic tip), a hook knife, a triangle tip knife, a Flush knife (whose tool bit is provided with a flushing hole), and the like. Each knife has its own features.

A rod-like electrode of the needle-knife can quickly dot to perform marking and cut a mucous membrane. A tool bit of the IT-knife is protected by a ceramic insulator, to avoid cutting an unnecessary part when dissecting a mucous membrane and prevent perforation and bleeding. When rotating to a proper angle, an L-shaped tool bit of the hook knife can quickly cut an edge of a lesion. Three radial electrodes of the triangle tip knife are beneficial to dotting to perform marking and burning a bleeding point to stop bleeding. The tool bit of the Flush knife is provided with a flushing hole, and can flush a bleeding point during a surgical process to improve vision.

In a process of performing ESD by a doctor, a lot of steps and instructions are involved. For example, an injection needle is used to inject normal saline to raise a lesion location, a needle-knife or a triangle tip knife is used for burning, dotting, and marking, a hook knife or a needle-knife is used for cutting an edge along the marks, an IT knife (having a ceramic tip) is used to dissect a tissue and burn a bleeding point to stop bleeding, a hemoclip is used to stop bleeding, hot biopsy forceps are used for electric coagulation, and an electrocautery snare is used for endoscopic variceal ligation and cutting.

A patent, entitled "HIGH-FREQUENCY KNIFE" and having a patent number: CN201380033286.7, of OLYMPUS MEDICAL SYSTEMS CORP. discloses a high-frequency knife, whose insulating tip is provided with a guide hole, where the guide hole is formed on a protruding portion and is kept from being blocked by the burnt tissue that has stuck to the outer peripheral surface of a tubular electrode.

A patent, entitled "HIGH-FREQUENCY TOOL FOR ENDOSCOPE" and having a patent number: CN201420273038.1, of ALTON (SHANGHAI) MEDICAL INSTRUMENTS CO., LTD. discloses a high-frequency tool for an endoscope, where a flushing hole is formed in the tool bit.

A patent, entitled "COMBINED ELECTROTOME" and having a patent number: CN201410281645.7, of HANGZHOU AGS MEDTECH CO., LTD. discloses a combined electrotome, where a tool bit portion includes at least two or more tool bits that can move or rotate relative to each other.

Therefore, in a process of performing surgery, a doctor replaces instruments according to requirements of the surgery, to satisfy requirements of respective steps. However, frequent instrument replacement is cumbersome and time-consuming, and is not beneficial to the surgery on a patient.

SUMMARY OF THE INVENTION

To resolve the foregoing problem, the present disclosure provides a multi-function high-frequency tool for an endoscope, integrating an IT knife, a needle-knife, and a water spraying function, to reduce a number of times of instrument replacement, save time and energy, and improve efficiency and safety.

To achieve the foregoing objective, the present invention uses the following technical solutions:

A multi-function high-frequency tool for an endoscope is provided, including an insert portion and a handle portion, where the insert portion includes an insulating tip, a first electrode having a needle-knife function, a second electrode having an IT-knife function, and a spray head; and the handle portion includes a first slider, a connector, an injection connector, and a second slider.

The second electrode has a hollow structure, and the first electrode extends through the second electrode; the proximal end of the first electrode is fixedly connected by means of a mandrel connecting member to the distal end of a mandrel; and the proximal end of the mandrel is connected to the first slider of the handle portion, and moves axially on the handle portion by means of the first slider, thereby actuating the first electrode to expose from and retract into the second electrode.

The spray head is fixedly connected by means of a hose connecting member to a hose, and several gaps formed between several troughs and the hose connecting member are provided on the spray head; and the hose is coated with an insulating sheath connected to the second slider, and actuates, by means of axial movement of the second slider, the insulating sheath to move axially, thereby causing the second electrode to expose from/retract into the insulating sheath.

The injection connector is in communication with the hose to form a liquid channel, and the injection connector can be connected to an injector or another standard connector providing normal saline. Finally, liquid is sprayed from a gap between the spray head and the hose connecting member. The sprayed liquid can flush a bleeding point and improve endoscopic vision, and can also flush the burnt tissue that has stuck to the second electrode and the radial electrode.

The outer diameter of the mandrel connecting member is larger than the aperture of a hollow portion inside the spray head, so that when the first electrode extends out by a distance, the mandrel connecting member is stopped by the spray head; the distal end of the second electrode is fixedly mounted inside the insulating tip, so that the second electrode whose distal end is fixedly provided with the insulating tip forms an IT knife having an insulating tip; and the first electrode, the second electrode, the mandrel, and the mandrel connecting member are all conductors, and the mandrel is connected to a high-frequency power supply through the connector of the handle portion.

In a preferable solution, the hollow portion is provided inside the spray head, four troughs are provided outside the spray head, and a protrusion is formed between two adjacent troughs; the proximal end of second electrode is nested inside the hollow portion of the spray head and is integrally connected to the spray head; and the spray head is integrally connected to the hose through the hose connecting member, and gaps are formed between the four troughs on the spray head and the hose connecting member.

In a preferable solution, a hollow portion is provided inside the radial electrode, four concave arc portions are provided outside the radial electrode, and two adjacent concave arc portions form a protrusion; and the second electrode extends through the hollow portion of the radial electrode and is integrally connected to the radial electrode. Such structural design increases an area of the radial electrode in contact with the tissue in a vertical direction and improves cutting efficiency.

In a preferable solution, surfaces of the four protrusions each formed by every two adjacent troughs on the spray head are all circular arc surfaces, and circular arcs of the four protrusions on a cross section have the same curvature.

In a preferable solution, a connection manner between the proximal end of the second electrode and the spray head is gluing or interference-fitting.

In a preferable solution, a connection manner between the spray head and the hose connecting member and a connection manner between the hose connecting member and the hose are gluing, interference-fitting, or welding.

In a preferable solution, a connection manner between the first electrode and the mandrel connecting member and a connection manner between the mandrel connecting member and the mandrel are mechanical crimping, laser welding, or brazing.

In a preferable solution, a connection manner between the second electrode and the radial electrode is laser welding, brazing, or gluing.

In a preferable solution, the hose is a flexible hose, and the proximal end of the flexible hose is connected to the injection connector.

In a preferable solution, a plane of the distal end of the hose connecting member is lower than a plane of the distal end of the insulating sheath.

In a preferable solution, the spray head is a spray apparatus made of an insulating material.

Compared with the prior art, the present invention has the following beneficial effects:

The present invention uses the foregoing technical solutions, where the first electrode having a needle-knife function implements functions such as quick dotting to perform marking and cutting a mucous membrane; the second electrode having an IT-knife function is additionally provided with an insulating tip on its distal end and implements functions such as dissecting the tissue and burning a bleeding point to stop bleeding; and a water spraying function is implemented: a liquid is sprayed from a gap between the spray head and the hose connecting member, and the sprayed liquid can flush a bleeding point and improve endoscopic vision, and can also flush the burnt tissue that has stuck to the second electrode and the radial electrode.

Therefore, according to the foregoing structure, a doctor may extend out a needed electrode according to requirements. The water spraying function can be implemented to not only flush the bleeding point, but also flush the second electrode and the radial electrode, thereby saving time for replacing instruments and extracting an electrosurgical knife to wash a tool bit.

Reference signs: insert portion 1, insulating tip 101, first electrode 102, radial electrode 103, hollow portion 103-1, concave arc portion 103-2, protrusion 103-3, second electrode 104, spray head 105, hollow portion 105-1, trough 105-2, protrusion 105-3, gap 105-4, hose connecting member 106, insulating sheath 107, hose 108, mandrel connecting member 109, mandrel 110, handle portion 2, handle 201, first slider 202, connector 203, injection connector 204, outer sheath 205, second slider 206.

DESCRIPTION OF THE EMBODIMENTS

Specific implementations of the present invention are described in detail below with reference to the accompanying drawings.

Figure 1:
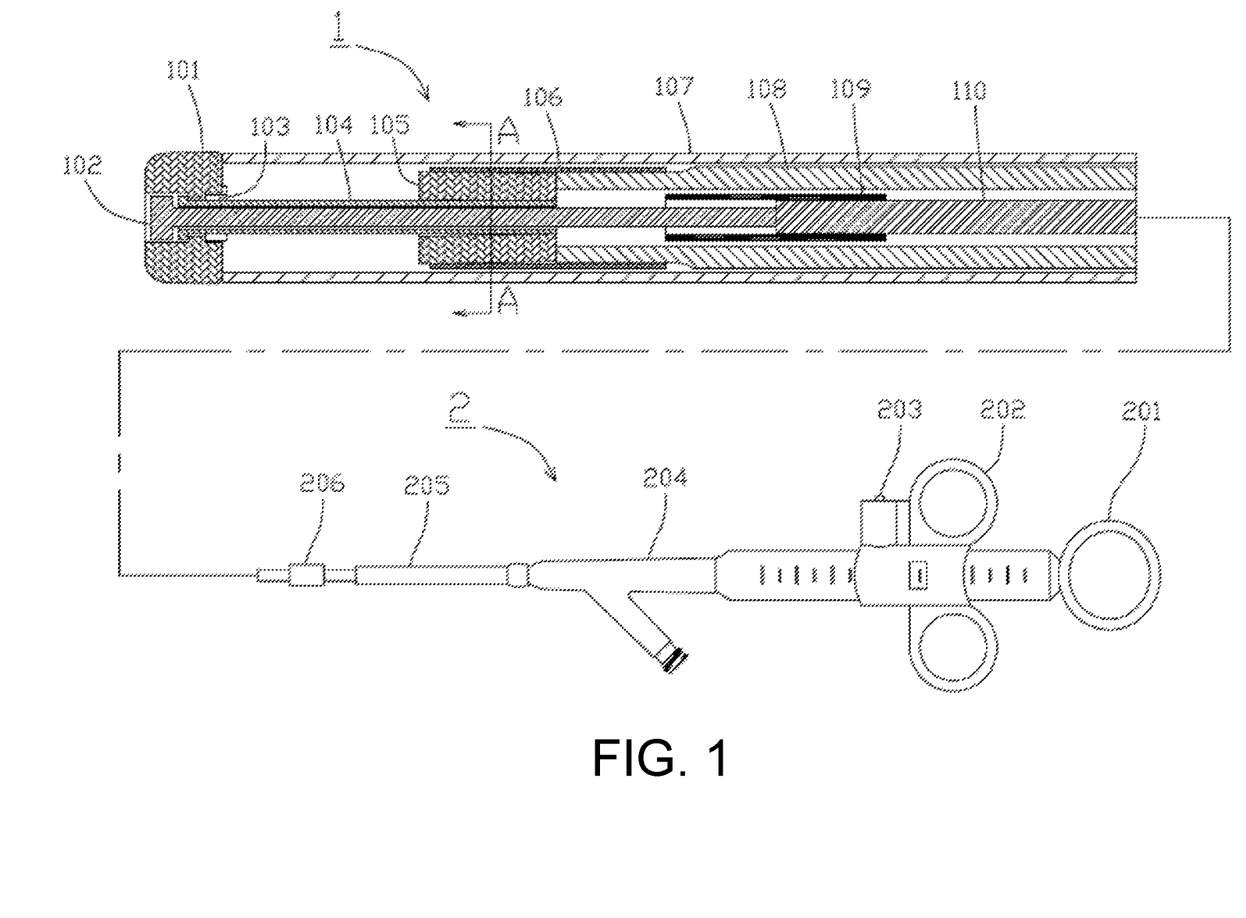
FIG. 1 is an overall schematic structural diagram of the present invention.

As shown in FIG. 1 to FIG. 6, this embodiment provides a specific embodiment of a multi-function high-frequency tool for an endoscope. As shown in FIG. 1, the multi-function high-frequency tool for an endoscope includes an insert portion 1 and a handle portion 2, where the insert portion 1 includes an insulating tip 101, a first electrode 102 having a needle-knife function, a second electrode 104 having an IT-knife function, a radial electrode 103, a spray head 105, a hose connecting member 106, an insulating sheath 107, a hose 108, a mandrel connecting member 109, and a mandrel 110; the handle portion 2 includes a handle 201, a first slider 202, a connector 203, an injection connector 204, an outer sheath 205, and a second slider 206; the second electrode 104 has a hollow structure, and the first electrode 102 extends through the second electrode 104; the proximal end of the first electrode 102 is integrally connected by means of a mandrel connecting member 109 to the distal end of a mandrel 110; and the proximal end of the mandrel 110 is connected to the first slider 202 of the handle portion 2, and moves axially on the handle portion 2 by means of the first slider 202, thereby actuating the first electrode 102 to expose from and retract into the second electrode 104. Refer to the structural schematic diagram of extending the first electrode 102 out in FIG. 2 for details.

Figure 4:
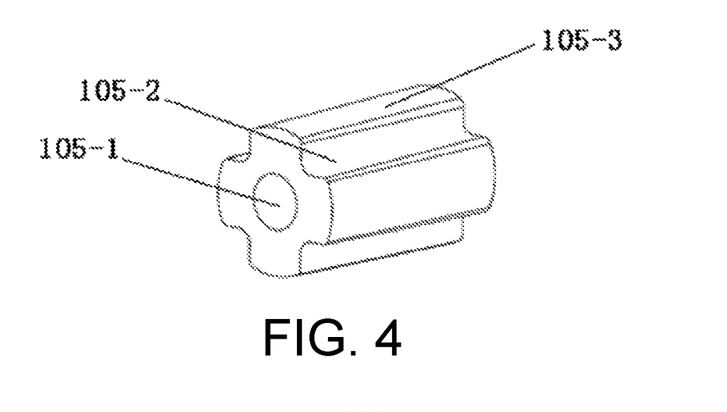
FIG. 4 is a schematic structural diagram of a spray head in the present invention.
Figure 5:
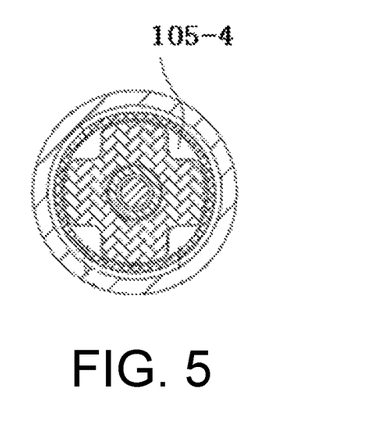
FIG. 5 is an enlarged schematic diagram of a cross section along an A-A line in FIG. 1.

As shown in FIG. 4, the hollow portion 105-1 is provided inside the spray head 105, four troughs 105-2 are provided outside the spray head 105, and a protrusion 105-3 is formed between two adjacent troughs 105-2. Surfaces of the four protrusions 105-3 each formed by every two adjacent troughs on the spray head 105 are all circular arc surfaces, and circular arcs of the four protrusions on a cross section have the same curvature. The proximal end of second electrode 104 is nested inside the hollow portion 105-1 of the spray head 105 and is integrally connected to the spray head 10 in an interference-fitting manner. The spray head 105 is integrally connected by means of the hose connecting member 106 to the hose 108. A connection manner between the spray head 105 and the hose connecting member 106 is gluing or interference-fitting. A connection manner between the hose connecting member 106 and the hose 108 is gluing, welding, or interference-fitting. Four gaps 105-4 are formed between 4 troughs 105-2 on the spray head 105 and the hose connecting member 106. Refer to the enlarged schematic diagram of a liquid outlet shown in FIG. 5.

The hose 108 is coated with an insulating sheath 107 connected to the second slider, and actuates, by means of axial movement of the second slider 206, the insulating sheath 107 to move axially, thereby causing the second electrode 104 to expose from/retract into the insulating sheath 107. Refer to the structural schematic diagram of extending the second electrode 104 out in FIG. 3 for details.

The hose 108 is a flexible hose. The injection connector 204 is in communication with the hose 108 to form a liquid channel, and the injection connector 204 can be connected to an injector or another standard connector providing normal saline.

Finally, liquid is sprayed from a gap between the spray head 105 and the hose connecting member 106. Refer to FIG. 4 for the spray head 105. Refer to the cross section alone an A-A line in FIG. 5 for the liquid outlet. The sprayed liquid can flush a bleeding point and improve endoscopic vision, and can also flush the burnt tissue that has stuck to the second electrode 104 and the radial electrode 103.

Figure 2:
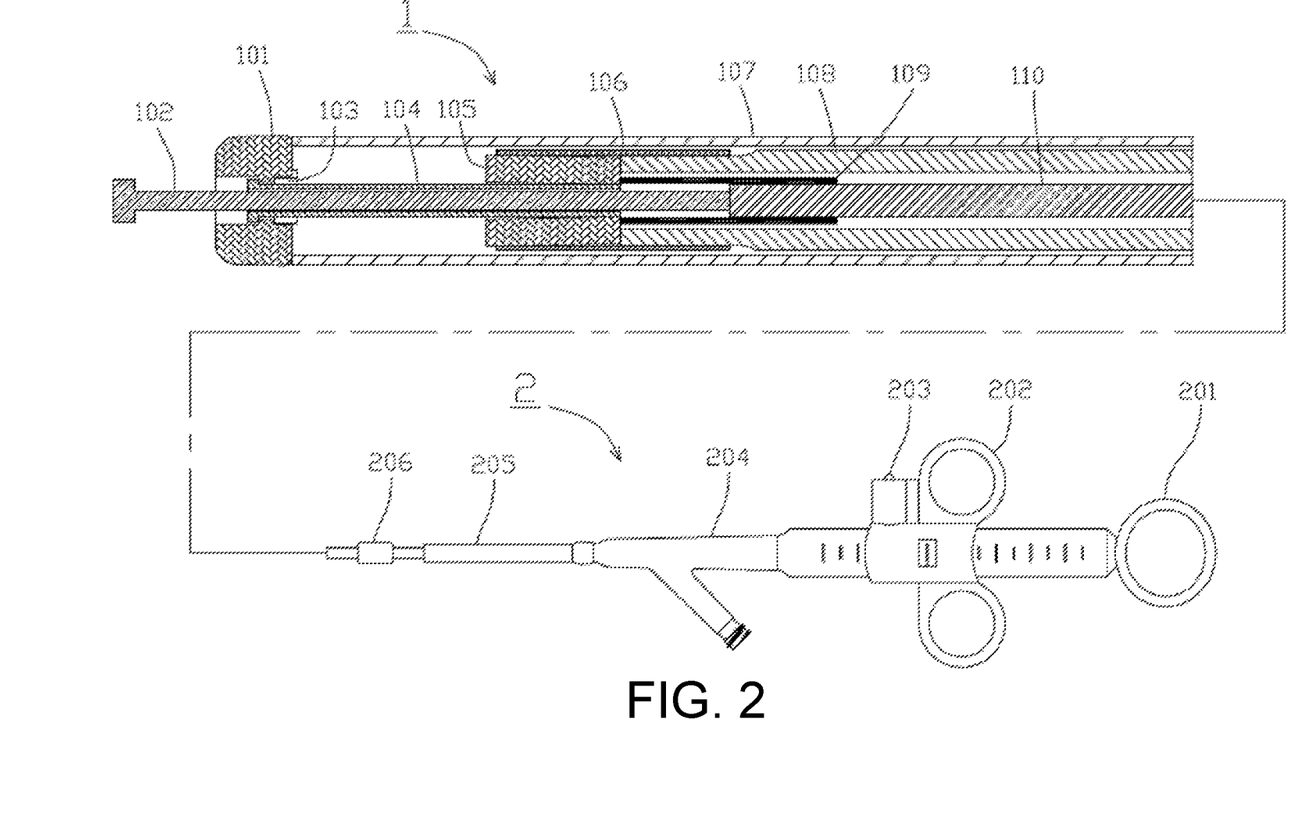
FIG. 2 is a schematic structural diagram of extending a first electrode out in the present invention.
Figure 3:
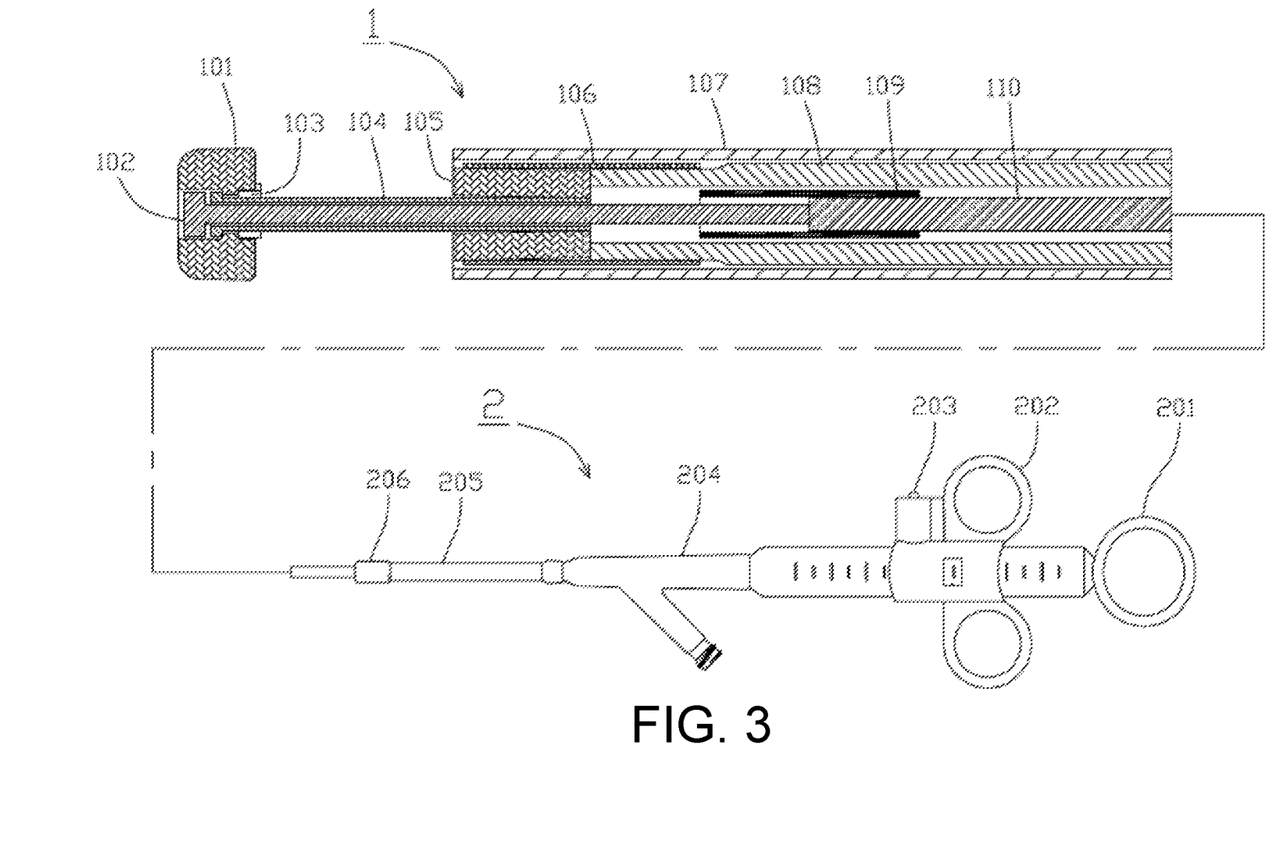
FIG. 3 is a schematic structural diagram of extending a second electrode out in the present invention.

As shown in FIG. 1 to FIG. 3, the outer diameter of the mandrel connecting member 109 is larger than the aperture of a hollow portion 105-1 inside the spray head 105, so that when the first electrode 102 extends out, the mandrel connecting member 109 is stopped by the spray head 105, deciding an extension length of the first electrode 102.

An insulating tip 101 is fixedly mounted between the second electrode 104 and the radial electrode 103. The first electrode 102, the second electrode 104, the mandrel 110, and the mandrel connecting member 109 are all conductors, and the mandrel 110 is connected to a high-frequency power supply through the connector 203 of the handle portion 2.

Figure 6:
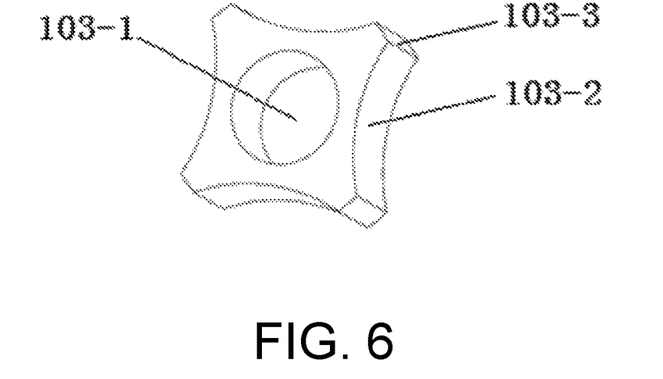
FIG. 6 is a schematic structural diagram of a radial electrode in the present invention.

As shown in FIG. 6, a hollow portion 103-1 is provided inside the radial electrode 103, four concave arc portions 103-2 are provided outside the radial electrode 103, and two adjacent concave arc portions 103-2 form a protrusion 103-3; and the second electrode 104 extends through the hollow portion 103-1 of the radial electrode 103 and is integrally connected to the radial electrode 103 in a laser welding manner. Such structural design increases an area of the radial electrode in contact with the tissue in a vertical direction and improves cutting efficiency.

The first electrode 102 is connected to the mandrel connecting member 109 in a mechanical crimping, laser welding, or brazing manner, and the mandrel connecting member 109 is connected to the mandrel 110 in a mechanical crimping, laser welding, or brazing manner.

A plane of the distal end of the hose connecting member 106 is lower than a plane of the distal end of the insulating sheath 107. The spray head 105 is a spray apparatus made of an insulating material.

The foregoing technical solutions are used, where the first electrode 102 having a needle-knife function implements functions such as quick dotting to perform marking and cutting a mucous membrane; the second electrode 104 having an IT-knife function is additionally provided with an insulating tip 101 on its distal end and implements functions such as dissecting the tissue and burning a bleeding point to stop bleeding; and a water spraying function is implemented: a liquid is sprayed from a gap between the spray head 105 and the hose connecting member 106, and the sprayed liquid can flush a bleeding point and improve endoscopic vision, and can also flush the burnt tissue that has stuck to the second electrode 104 and the radial electrode 103.

Therefore, according to the foregoing structure, a doctor may extend out a needed electrode according to requirements. The water spraying function can be implemented to not only flush the bleeding point, but also flush the second electrode 104 and the radial electrode 103, thereby saving time for replacing instruments and extracting an electrosurgical knife to wash a tool bit.

Basic principles and major feature of the present invention and advantages of the present invention are illustrated and described. It should be understood by persons skilled in the art that the present invention is not limited by the foregoing embodiments, and the foregoing embodiments and description merely describe the principles of the present invention, various alterations and improvements can be made on the present invention without departing from the spirit and scope of the present invention, and all the alterations and improvements fall within the protection scope of the present invention. The protection scope of the present invention is defined by the attached claims and the equivalent thereof.

What is claimed is:

1. A multi-function high-frequency tool for an endoscope, comprising:
an insert portion; and
a handle portion,
wherein the insert portion comprises:
    an insulating tip;
    a first electrode having a needle-knife function;
    a second electrode having an IT-knife function; and
    a spray head,
wherein the handle portion comprises:
    a first slider;
    a connector;
    an injection connector; and
    a second slider;
the second electrode has a hollow structure, and the first electrode extends through the second electrode; a proximal end of the first electrode is fixedly connected to a distal end of a mandrel through a mandrel connecting member; a proximal end of the mandrel is connected to the first slider of the handle portion, and drives the first electrode to be exposed from and retracted into the second electrode as the first slider moves axially on the handle portion;
the spray head is fixedly connected to a hose through a hose connecting member, and a plurality of gaps formed between a plurality of troughs and the hose connecting member are provided on the spray head;
the hose is coated with an insulating sheath connected to the second slider, and drives the insulating sheath to move axially with an axial movement of the second slider, thereby causing the second electrode to expose from and retract into the insulating sheath;
the injection connector is in communication with the hose to form a liquid channel, and an outer diameter of the mandrel connecting member is larger than an aperture of a hollow portion inside the spray head, so that when the first electrode extends out by a distance, the mandrel connecting member is stopped by the spray head;
a proximal end of the second electrode is nested inside the hollow portion of the spray head and is fixedly connected to the spray head; a distal end of the second electrode is fixedly mounted inside the insulating tip, so that the second electrode whose distal end is fixedly provided with the insulating tip forms an IT knife comprising an insulating tip; and the first electrode, the second electrode, the mandrel, and the mandrel connecting member are all conductors, and the mandrel is connected to a high-frequency power supply through the connector of the handle portion.

2. The multi-function high-frequency tool for an endoscope according to claim 1, wherein the hollow portion is provided inside the spray head, wherein the plurality of troughs comprises four troughs provided outside the spray head, and protrusions are formed between each adjacent troughs.

3. The multi-function high-frequency tool for an endoscope according to claim 1, wherein a radial electrode is fixedly mounted between the distal end of the second electrode and the insulating tip, a hollow portion is provided inside the radial electrode, four concave arc portions are provided outside the radial electrode, and two adjacent concave arc portions of the four concave arc portions form a protrusion; and the second electrode extends through the hollow portion of the radial electrode and is fixedly connected to the radial electrode.

4. The multi-function high-frequency tool for an endoscope according to claim 2, wherein surfaces of the protrusions on the spray head are all circular arc surfaces, and the circular arc surfaces of the protrusions on a cross section have a same curvature.

5. The multi-function high-frequency tool for an endoscope according to claim 1, wherein a connection manner between the proximal end of the second electrode and the spray head is gluing or interference-fitting.

6. The multi-function high-frequency tool for an endoscope according to claim 1, wherein a connection manner between the spray head and the hose connecting member and a connection manner between the hose connecting member and the hose are gluing, interference-fitting, or welding.

7. The multi-function high-frequency tool for an endoscope according to claim 1, wherein a connection manner between the first electrode and the mandrel connecting member and a connection manner between the mandrel connecting member and the mandrel are mechanical crimping, laser welding, or brazing.

8. The multi-function high-frequency tool for an endoscope according to claim 3, wherein a connection manner between the second electrode and the radial electrode is laser welding, brazing, or gluing.

9. The multi-function high-frequency tool for an endoscope according to claim 1, wherein the hose is a flexible hose, and a proximal end of the flexible hose is connected to the injection connector.

\* \* \* \* \*